United States Patent
Bassin

(10) Patent No.: US 9,205,210 B2
(45) Date of Patent: Dec. 8, 2015

(54) ADJUSTMENT OF TARGET VENTILATION IN A SERVOVENTILATOR

(75) Inventor: David John Bassin, Coogee (AU)

(73) Assignee: ResMed Limited (AU)

( * ) Notice: Subject to any disclaimer, the term of this patent is extended or adjusted under 35 U.S.C. 154(b) by 1303 days.

(21) Appl. No.: 11/574,057

(22) PCT Filed: Sep. 2, 2005

(86) PCT No.: PCT/AU2005/001336
§ 371 (c)(1),
(2), (4) Date: Feb. 21, 2007

(87) PCT Pub. No.: WO2006/024107
PCT Pub. Date: Mar. 9, 2006

(65) Prior Publication Data
US 2009/0013999 A1    Jan. 15, 2009

(30) Foreign Application Priority Data
Sep. 3, 2004    (AU) ................................ 2004905022

(51) Int. Cl.
*A61M 16/00* (2006.01)

(52) U.S. Cl.
CPC ............ *A61M 16/00* (2013.01); *A61M 16/0066* (2013.01); *A61M 2016/0021* (2013.01); *A61M 2016/0027* (2013.01); *A61M 2016/0039* (2013.01); *A61M 2205/502* (2013.01)

(58) Field of Classification Search
CPC ............ A61M 16/00; A61M 16/0003; A61M 16/0051–16/0072; A61M 16/20–16/205; A61M 2016/0015–2016/0033
USPC .............. 128/204.18–204.23, 204.26, 200.24
See application file for complete search history.

(56) References Cited

U.S. PATENT DOCUMENTS

| | | | |
|---|---|---|---|
| 5,117,819 A | 6/1992 | Servidio et al. | |
| 5,494,028 A * | 2/1996 | DeVries et al. | 128/205.24 |
| 5,682,878 A | 11/1997 | Ogden | |
| 6,401,713 B1 | 6/2002 | Hill et al. | |
| 6,467,477 B1 | 10/2002 | Frank et al. | |
| 6,532,956 B2 * | 3/2003 | Hill | 128/204.18 |
| 6,532,957 B2 | 3/2003 | Berthon-Jones | |

(Continued)

FOREIGN PATENT DOCUMENTS

| | | |
|---|---|---|
| JP | 2001-286564 | 10/2001 |
| WO | 0202169 | 1/2002 |
| WO | 03030804 | 4/2003 |
| WO | 2003075991 | 9/2003 |

OTHER PUBLICATIONS

European Search Report dated Oct. 24, 2012.

(Continued)

*Primary Examiner* — Rachel Young
(74) *Attorney, Agent, or Firm* — Lerner, David, Littenberg, Krumholz & Mentlik, LLP

(57) ABSTRACT

A servoventilator control slowly changes the target ventilation over a period of time, according to a preprogrammed schedule adapted to be set by the physician. Preferably, the target ventilation stays constant at an initial target ventilation for an initial hold time, and then increases at a constant rate until it reaches a final target ventilation, whereupon it stays constant thereafter. If the pressure support level is too high, possibly indicating glottic or upper airway closure, the rate of increase of target ventilation may be lowered or the final target ventilation not reached.

10 Claims, 2 Drawing Sheets

(56) References Cited

U.S. PATENT DOCUMENTS

Figure 1:
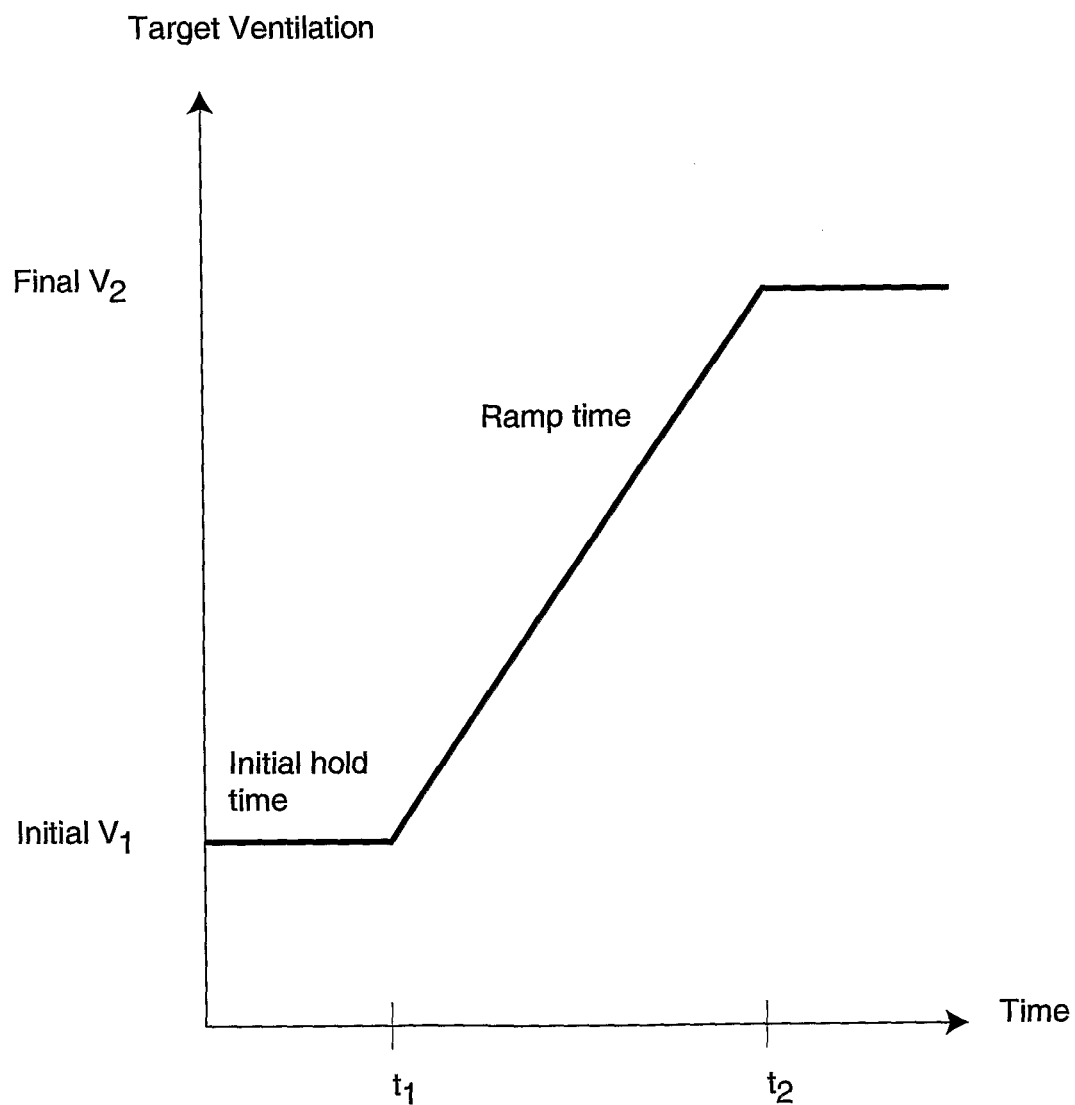

| | | | |
|---|---|---|---|
| 6,581,595 B1* | 6/2003 | Murdock et al. | 128/204.18 |
| 6,644,312 B2 | 11/2003 | Berthon-Jones et al. | |
| 6,920,877 B2* | 7/2005 | Remmers et al. | 128/204.18 |
| 7,013,892 B2* | 3/2006 | Estes et al. | 128/204.18 |
| 2001/0027792 A1* | 10/2001 | Berthon-Jones et al. | 128/204.23 |
| 2004/0187870 A1* | 9/2004 | Matthews et al. | 128/204.22 |

OTHER PUBLICATIONS

Notice of Reasons for Rejection, Patent Application No. P2007-529304, Japanese Patent Office, Dec. 21, 2010.

International Search Report & Written Opinion for Application No. PCT/AU05/001336 dated Sep. 30, 2005.

* cited by examiner

ADJUSTMENT OF TARGET VENTILATION IN A SERVOVENTILATOR

This application claims the benefit of the filing of Australian Provisional application AU 2004/905022 filed Sep. 3, 2004.

FIELD OF THE INVENTION

The present invention relates to the field of ventilatory assistance, and in particular, to methods and apparatus for determining suitable ventilator settings in patients with alveolar hypoventilation during sleep, and for delivery of those settings.

BACKGROUND OF THE INVENTION

In the field of noninvasive ventilation, for example as described in U.S. Pat. No. 6,532,957, a problem arises particularly in patients newly introduced to servoventilation. The patient's arterial CO2 partial pressure (PCO2) may be well above the value preferred by the clinician; for example, the PCO2 may be 60 mm Hg, and the clinician would prefer to stabilize it at 45 mm Hg. This would require the patient's alveolar ventilation to be increased by a factor of approximately 60/45=4/3. Yet if the clinician sets the target ventilation of the servoventilator to 4/3 of the patient's current ventilation, such a large increase in ventilation, if it occurs immediately, is likely to abolish all respiratory drive and much of the upper airway drive (leading to problems with upper airway obstruction). It may cause glottic closure, preventing the ventilation from increasing to the target level, despite the ventilator delivering the maximum level of pressure support for which it is programmed, which may lead to arousal from sleep. If the arterial pH is relatively normal at the beginning of therapy, indicating a metabolic compensation for a relatively chronic respiratory acidosis, a sudden large increase in ventilation would result in a marked alkalosis, with undesirable electrolyte shifts, including hypokalaemia, with the potential for inducing cardiac arrhythmias.

For these reasons a progressive increase of target ventilation over a period of time, typically several days or weeks, is desirable. This might be achieved by frequent manual changes of the target ventilation, but this would be inconvenient, since the patient is likely to be at home at this stage.

BRIEF DESCRIPTION OF THE INVENTION

In accordance with my invention, a servoventilator incorporates a mechanism for slowly changing the target ventilation over a period of time, according to a preprogrammed schedule set by the physician. In most cases the intention will be that the target ventilation increases over a period of time, from a first level to a second level, then stay at the second level thereafter. This increase could occur according to any arbitrary increasing function of time.

In one form of my invention, the target ventilation stays constant at a first level, $V_1$ (the initial target ventilation) for a fixed period of time (the initial hold time) until time $t=t_1$, which might be zero, then increases at a constant rate until it reaches a second level, $V_2$ (the final target ventilation), whereupon it stays constant thereafter.

The rate of increase, R may be calculated from the initial target ventilation $V_1$, the final target ventilation $V_2$, and a target ventilation ramp time $t_r$, all these settings being entered by the clinician using the following equations:

$$t_r = t_2 - t_1$$

$$R = \frac{V_2 - V_1}{t_r}$$

Various constraints may be added to modify the rate of increase of target ventilation. For example, if the pressure support level is too high, possibly indicating glottic or upper airway closure, the rate of increase of target ventilation may be lowered or even set to zero temporarily, so it takes longer to reach the final target ventilation, or in some cases the final target ventilation may never be achieved.

DETAILED DESCRIPTION OF A PREFERRED EMBODIMENT

FIG. 1 illustrates an embodiment of my invention. The x-axis shows time, the y-axis shows ventilator target ventilation.

Figure 2:
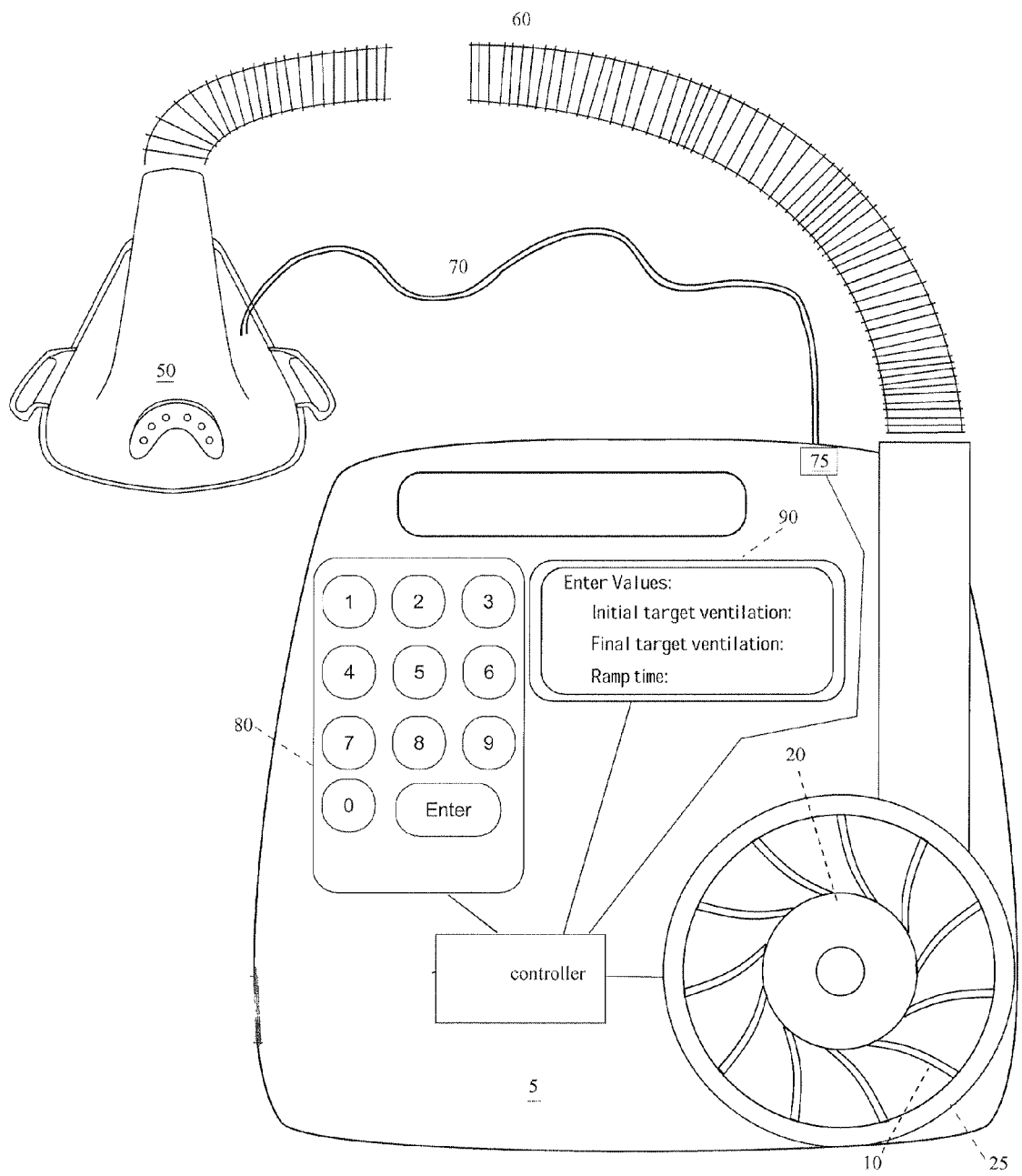

FIG. 2 illustrates servo-ventilator apparatus 5 suitable to perform the invention. An electric motor 20 has an impeller 10 and is under the control of a controller circuit 40. In use the motor and impeller is housed in a volute 25, which in use allows a flow of pressurized air to pass along the air delivery conduit 60 to a suitable patient interface 50. The patient interface 50 may be a nasal mask, or nose and mouth mask, a full-face mask or some other suitable device. A pressure sense tube 70 between the patient interface 50 and a pressure sensor 75 allows the controller 40 to sense pressure in the patient interface 50. The controller 40 can also determine the flow rate and of air along the air delivery conduit 60 via a flow sensor (not shown). The apparatus includes a display 90 and keyboard 80 which allow someone, for example a clinician, to set appropriate target ventilators and ramp times in accordance with an embodiment of the invention.

The determination of target ventilation settings may be accomplished as described in U.S. Pat. No. 6,644,312, the disclosure of which is incorporated by reference. In particular, suitable initial target ventilator settings for use with a servoventilator may be determined by measurements and observations made on the subject patient while awake during a learning period. Or, the target ventilation may be a fixed percentage of an average ventilation taken over a portion of the learning period. During the learning period the servo-control of ventilation is disabled, and the device is set to deliver a fixed minimum degree of support, typically 6 cmH2O chosen to make the patient feel comfortable. During this learning period, ventilation is measured and oxygen saturation levels may be measured by an oximeter. A target ventilation for use during sleep is selected or determined based on the ventilation measurements and optionally oxygen saturation measurements. Where the PCO2 of the subject patient would be higher than desired by the clinician, a final target ventilation can be determined by multiplying an initial target ventilation by the ratio of the PCO2 value to a desired PCO2 value.

A clinical algorithm embodying the invention is:
  (i) use a suitable ventilator to learn the patient's awake ventilation (for example according to U.S. Pat. No. 6,644,312;
  (ii) set the initial target ventilation to a proportion of this ventilation;
  (iii) set the final target ventilation to the initial target ventilation multiplied by the ratio of the current PCO2 to the desired PCO2

(iv) set the target ventilation ramp time to some suitable value, depending on the clinical urgency of lowering the PCO2 and the amount by which it is desired to lower the PCO2 (all else being equal, larger falls might be expected to take longer)

A similar principle can be applied to conventional bilevel ventilation. The pressure support level can be programmed, after an initial hold time, to increase at a certain rate until it reaches a final pressure support level.

Thus in accordance with my invention there is provided a method of non-invasive ventilation of a patient comprising the steps of:
(i) ventilating a patient at a first level of ventilation for a first duration; and
(ii) At the expiration of the first duration, changing the level of ventilation from the first level to a second level over a second duration.

In one form of the invention, the second duration may be several weeks. In a preferred form, the change in level of ventilation is an increase. In one preferred form of the invention, the change in level of ventilation is automatically controlled.

Although my invention has been described with reference to particular embodiments, it is to be understood that these embodiments are merely illustrative of the application of the principles of the invention. Numerous modifications may be made therein and other arrangements may be devised without departing from the spirit and scope of the invention.

The invention claimed is:

1. A servoventilator apparatus for delivering pressure support ventilation to a patient with alveolar hypoventilation during sleep comprising:
a controller circuit;
an electric motor having an impeller under the control of the controller circuit that allows a flow of pressurized air to pass along an air delivery conduit to a patient interface to deliver the pressure support ventilation; and
means to allow setting a final target ventilation and a target ventilation ramp time;
the controller being operative to servo-ventilate the patient through said patient interface with said pressurized air in accordance with a set target ventilation, the target ventilation being a volume of gas to be breathed by the patient per unit time,
wherein the controller changes the set target ventilation according to a programmed schedule from an initial target ventilation to the final target ventilation;
the target ventilation increasing at a determined rate over the target ventilation ramp time until it reaches the final target ventilation whereupon it stays constant thereafter,
the ventilation ramp time being at least days long to prevent glottic closure or cessation of respiratory drive.

2. The servoventilator apparatus of claim 1 wherein the target ventilation stays constant at the initial target ventilation level for a predetermined initial hold time.

3. The servoventilator apparatus of either of claims 1 and 2 wherein the controller further provides for the setting of the initial target ventilation to a proportion of a patient's awake ventilation; setting of the final target ventilation to the initial target ventilation multiplied by the ratio of a current $PCO_2$ value to a desired $PCO_2$ value; and setting of the target ventilation ramp time to a value depending on the clinical urgency of lowering the PCO2 and the amount by which it is desired to lower the PCO2.

4. The servoventilator apparatus of claim 1 wherein the controller modifies the determined rate of increase of the target ventilation if the pressure support level is too high to prevent glottic closure or cessation of respiratory drive.

5. The servoventilator apparatus of claim 4 wherein the determined rate of increase of the target ventilation is lowered so it takes longer to reach the final target ventilation.

6. The servoventilator apparatus of claim 4 wherein the determined rate of increase of the target ventilation is changed to zero temporarily.

7. The servoventilator apparatus of claim 4 wherein the determined rate of increase is changed such that the final target ventilation is never reached.

8. The servoventilator apparatus of claim 1 wherein the target ventilation increases at a constant rate during the target ventilation ramp time.

9. The servoventilator apparatus of claim 1, wherein the target ventilation is a minute ventilation.

10. The servoventilator apparatus of claim 1, wherein the target ventilation is a tidal volume.

* * * * *